United States Patent [19]
Kato et al.

[11] Patent Number: 5,095,034
[45] Date of Patent: Mar. 10, 1992

[54] PHARMACEUTICAL COMPOSITION FOR PREVENTING AND TREATING THROMBOSIS

[75] Inventors: Koichi Kato, Kawanishi; Yukio Shimomura, Suita; Norihiko Moriya, Kawabe; Koichi Matsumura, Ibaraki, all of Japan

[73] Assignee: Takeda Chemical Industries, Ltd., Osaka, Japan

[21] Appl. No.: 515,407

[22] Filed: Apr. 27, 1990

[30] Foreign Application Priority Data

Apr. 28, 1989 [JP] Japan .................... 1-109789

[51] Int. Cl.$^5$ ............................ A61K 31/34
[52] U.S. Cl. ..................... 514/474; 514/822
[58] Field of Search ............. 514/474, 822; 549/315

[56] References Cited

U.S. PATENT DOCUMENTS 4,329,290  5/1982  Sawyer et al. .................. 549/316

FOREIGN PATENT DOCUMENTS 0228273  7/1987  European Pat. Off. .
0295842  12/1988  European Pat. Off. .

OTHER PUBLICATIONS

Medical Hypotheses, vol. 19, 1986, pp. 345–357, McCarthy et al., "An Antithrombotic Role for Nutritional Antioxidants".
Chemical Abstracts, vol. 106, No. 21, May 25, 1987, p. 72, Abstract No. 169048q.
Chemical Abstracts, vol. 97, No. 7, Aug. 16, 1982, p. 631, Abstract No. 55611h.

Primary Examiner—Frederick E. Waddell
Assistant Examiner—Raymond J. Henley, III
Attorney, Agent, or Firm—Wenderoth, Lind & Ponack

[57] ABSTRACT

A pharmaceutical composition for preventing and treating thrombosis containing, as an active component, a saccharoascorbic acid derivative such as 2,3-di-O-benzyl-D-glucosaccharoascorbic acid n-octadecanethiol ester is disclosed.

8 Claims, No Drawings

PHARMACEUTICAL COMPOSITION FOR PREVENTING AND TREATING THROMBOSIS

FIELD OF THE INVENTION

The present invention relates to a pharmaceutical composition for preventing and treating thrombosis which contains a saccharoascorbic acid derivative as an active component. More particularly, the present invention provides a pharmaceutical composition which prevents and treats thrombosis by the action of the saccharoascorbic acid derivative on vascular endothelial cells to accelerate fibrinolysis reaction.

BACKGROUND OF THE INVENTION

Blood circulates in health blood vessels, while always maintaining fluidity. However, in morbid states such as inflammation, injury, vascular endothelial disorders and the like, blood coagulation proceeds by a cascade reaction wherein various coagulation factors participate and, at the final stage thereof, conversion of fibrinogen into fibrin occurs to coagulate blood. A significant example thereof is intravascular coagulation and a representative typical example thereof is thrombosis. Fibrin deposited in a blood vessel clogs up the vessel, which occasionally causes mortal diseases such as myocardial infarction, brain infarction and the like.

It is known that there is an enzyme precursor, called plasminogen, in circulating blood and that the precursor is converted into plasmin due to restrictive decomposition by a plasminogen activator. Plasmin is a serine protease having affinity to fibrin which decomposes and dissolves fibrin. The series of these reactions is called a fibrinolysis reaction A drug, which can accelerate the fibrinolysis reaction, dissolves and removes fibrin once it is formed and, therefore, it is effective for treatment of thrombosis and prevention of a recurrence thereof.

Hitherto, plasminogen activator preparations or protein preparations such as urokinase, tissue plasminogen activator, streptokinase, prourokinase and the like have been used as drugs which accelerate the fibrinolysis reaction by activating the enzyme precursor, plasminogen, to form plasmin [Biochim. Biophys. Acta, 24, 278 (1957); J. Biol. Chem., 256, 7035 (1981); Trends. Biochem. Sci., 4, 1 (1979); and Blood, 67, 1215 (1986)].

A pharmaceutical composition for preventing and treating thrombosis comprising as an active component retinoyl L-ascorbate (Japanese Patent Laid Open Publication No. 66160/1988) and comprising as active components retinoic acid and L-ascorbic acid (Japanese Patent Laid Open Publication No. 13/1987) have also been known.

Further, it has been reported that steroids such as stanozolol and the like have antithrombotic activities [Fibrinolysis, Vol. 1, pp 29-32 (1987)].

However, these known drugs have various drawbacks. For example, the enzymatic preparations such as urokinase, tissue plasminogen activator and the like have a relatively short half life in blood and cause systemic hemorrhagic trend. Since streptokinase is a foreign protein derived from bacteria, it has immunogenicity. Regarding ascorbic acid, retinoic acid and the like, a high concentration of the drug is required for manifesting its activities. Further, steroids have strong side effects.

Thus, it is desired to develop a new drug for treating and preventing thrombosis which has improved activities with minimized side effects.

OBJECTS OF THE INVENTION

The main object of the present invention is to provide a novel pharmaceutical composition for preventing and treating thrombosis which can minimize the above drawbacks of the conventional drugs for preventing and treating thrombosis.

This object as well as other objects and advantages of the present invention will become apparent to those skilled in the art from the following description.

SUMMARY OF THE INVENTION

The present inventors have aimed at the fact that plasminogen activator produced by vascular endothelial cells acts on plasminogen to produce plasmin, and have widely investigated substances which can promote and/or induce the production of plasminogen activator by vascular endothelial cells. As a result, it has been found that saccharoascorbic acid derivatives have these activities.

Thus, according to the present invention, there is provided a pharmaceutical composition for preventing and treating thrombosis which comprises a compound of the formula (I):

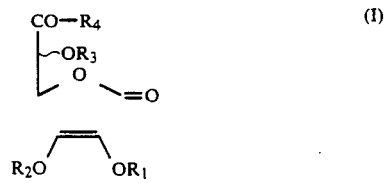

wherein $R_1$ and $R_2$ are hydrogen, or a straight or branched and optionally substituted hydrocarbon group having 6 to 24 carbon atoms, provided that at least one of $R_1$ and $R_2$ is other than hydrogen; $R_3$ is hydrogen or an acyl group; —CO—$R_4$ is an esterified carboxyl group, a thiol-esterified carboxyl group or an amidated carboxyl group; and ~ represents the absolute configuration of R or S, and a pharmaceutically acceptable carrier.

DETAILED DESCRIPTION OF THE INVENTION

The term "thrombosis" used herein means all morbidities accompanying intravascular coagulation of blood and all diseases caused by such a coagulation are included in the objective diseases of the present invention.

The hydrocarbon group having 6 to 24 carbon atoms of the saccharoascorbic acid derivative of the above formula (I) used in the present invention includes a straight, branched or cyclic alkyl group and an aralkyl group. These groups may be optionally substituted with halogen (e.g., fluorine, chlorine, bromine, iodine, etc.), carboxyl or its ester, carbamoyl, amino, hydroxy, phenyl, nitro, cyano, alkoxy having 1 to 4 carbon atoms, alkyl having 1 to 4 carbon atoms optionally substituted with halogen or the like.

The alkyl group having 6 to 24 carbon atoms is exemplified by hexyl, heptyl, octyl, nonyl, decyl, undecyl, dodecyl, tridecyl, tetradecyl, pentadecyl, hexadecyl, octadecyl, nonadecyl, icosyl, henicosyl, docosyl, tricosyl, tetracosyl, cyclohexyl, cycloheptyl, cyclooctyl, etc. Preferably a straight or branched alkyl group having 6 to 18 carbon atoms or a cycloalkyl having 6 to 8 carbon atoms are used.

The aralkyl group essentially has lower alkyl substituted with an aromatic group. Preferably the aralkyl group having 7 to 24 carbon atoms is used. The said lower alkyl is exemplified by methyl, ethyl, propyl, butyl, etc. It includes a straight or branched alkyl having 1 to 4 carbon atoms. The said aromatic group is exemplified by phenyl, etc.

In This invention at least one of $R_1$ and $R_2$ is preferably benzyl. More preferably both of $R_1$ and $R_2$ are benzyl.

Examples of the acyl group of $R_3$ include that having 1 to 18 carbon atoms such as formyl, acetyl, propionyl, butyryl, isobutyryl, valeryl, isovaleryl, pivaroyl, benzoyl and the like.

When the group —CO—$R_4$ is an esterified carboxyl group or a thiol-esterified carboxyl group, they are represented by the formulas —CO—O—$R_5$ and —CO—S—$R_6$, respectively, wherein $R_5$ and $R_6$ are a hydrocarbon group having 1 to 24 carbon atoms.

When the group —CO—$R_4$ is an amidated carboxyl group, it is represented by the formula

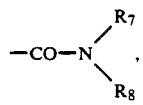

wherein $R_7$ and $R_8$ are the same or different and hydrogen or a hydrocarbon group having 1 to 24 carbon atoms, or $R_7$ and $R_8$ may together form —(CH$_2$)$_n$— (wherein n is an integer of 4 to 7). When $R_7$ and $R_8$ together form —(CH$_2$)$_n$—, the resulting ring can have one or more substituents such as halogen (e.g., fluorine, chlorine, bromine, iodine, etc.), carboxyl or its ester, carbamoyl, amino, hydroxy, phenyl, nitro, cyano, alkoxy having 1 to 4 carbon atoms, alkyl having 1 to 4 carbon atoms optionally substituted with halogen and the like. Preferably, —NR$_7$R$_8$ is —NH (C$_1$–C$_{24}$) alkyl —NH$_2$, or, when $R_7$ and $R_8$ forms a ring,

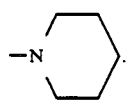

Examples of the hydrocarbon group of $R_5$, $R_6$, $R_7$ and $R_8$ include a straight or branched alkyl group having 1 to 24 carbon atoms, a cycloalkyl group having 3 to 8 carbon atoms, an alkenyl group having 1 to 24 carbon atoms, an alkynyl group having 1 to 24 carbon atoms, an aralkyl group having 7 to 24 carbon atoms, an aryl group having 5 to 24 carbon atoms and the like. These group may have one or more substituents such as halogen (e.g., fluorine, chlorine, bromine, iodine, etc.) carboxyl or its ester, carbamoyl, amino, hydroxy, phenyl, nitro, cyano, alkoxy having 1 to 4 carbon atoms, alkyl having 1 to 4 carbon atoms optionally substituted with halogen and the like.

Examples of the straight or branched alkyl group of 1 to 24 carbon atoms include methyl, ethyl, n-propyl, isopropyl, n-butyl, sec-butyl, tert-butyl, n-pentyl, isoamyl, tert-amyl, hexyl, heptyl, octyl, nonyl, decyl, undecyl, dodecyl, tridecyl, tetradecyl, pentadecyl, hexadecyl, octadecyl, nonadecyl, icosyl, henicosyl, docosyl, tricosyl, tetracosyl, etc.

Examples of the cycloalkyl group include those of 3 to 8 carbon atoms, e.g., cyclopropyl, cyclobutyl, cyclopentyl, cyclohexyl, cycloheptyl, cyclooctyl, etc.

Examples of the alkenyl group of 2 to 24 carbon atoms include vinyl, allyl, butenyl, pentenyl, hexenyl, heptenyl, octenyl, nonenyl, decenyl, undecenyl, dodecenyl, tridecenyl, tetradecenyl, pentadecenyl, heptadecenyl, octadecenyl, nonadecenyl, icosenyl, henicosenyl, docosenyl, tricosenyl, tetracosenyl, etc.

Examples of the alkynyl group having 2 to 24 carbon atoms include ethynyl, propynyl, butynyl, pentynyl, hexynyl, heptynyl, octynyl, nonynyl, decynyl, undecynyl, dodecynyl, tridecynyl, tetradecynyl, pentadecynyl, heptadecynyl, octadecynyl, nonadecynyl, icosynyl, henicosenyl, heicosynyl, tricosynyl, tetracosynyl, etc.

Examples of the aralkyl include alkyl groups of 1 to 4 carbon atoms substituted with an aryl group represented by phenyl, thienyl, pyridyl, naphthyl, etc. (e.g., benzyl, phenethyl, furfuryl, phenylpropyl, phenylbutyl, etc.).

Examples of the aryl group of 1 to 24 carbon atoms include carbocyclic aromatic compounds and heterocyclic aromatic compounds such as phenyl, furyl, thienyl, pyridyl, naphthyl, groups, etc.

Among the compounds of the formula (I), those having the esterified carboxyl group of —CO—O—$R_5$ wherein $R_1$ and $R_2$ are hydrogen or benzyl can be produced by the process disclosed in Japanese Patent Laid Open Publication No. 85970/1989 (EP-A-0 295 342).

The compound of this invention can be produced by using saccharoascorbic acid of the formula (II):

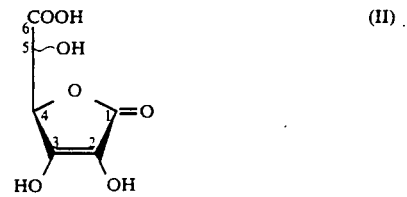

as a starting material.

In the formula (II), when the hydroxy group at the 5-position is located at the right side (R-configuration), the compound is L-gulosaccharoascorbic acid which is a known compound (for example, U.S. Pat. No. 2,428,438). When the hydroxy group at the 5-position is located at the left side (S-configuration), the compound is D-glucosaccharoascorbic acid and is prepared by treating 2-keto-D-glucaric acid (D-arabino-2-hexulosaric acid), or its 2,3-O-acetal or -ketal with an acid (Japanese Patent Laid Open Publication No. 228091/1987).

That is, the compound having the thiol-esterified carboxyl group of —CO—S—$R_6$ can be prepared according to the scheme 1:

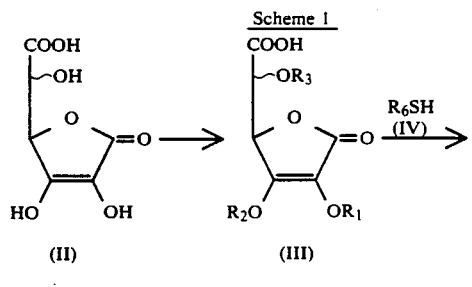

-continued
Scheme 1

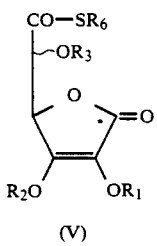

(V)

wherein R₁, R₂, R₃ and R₆ are as defined above.

As seen from the scheme 1, the compound (III) is reacted with the thiol of the formula (IV) to obtain the compound of the formula (V). Then, if necessary, the groups R₁, R₂ or R₃ can be removed.

The production of the compound (III) from the compound (II) can be carried out according to a known method, for example, that described in EP-A-0 295 842 or according to the methods as described in the schemes 4 and 5 hereinafter.

The production of the compound (V) by the reaction of the compound (III) with the compound (IV) can be carried out according to a known thiol ester synthesis.

For example, the reaction can be carried out using a carboxyl-activating reagent in an organic solvent. Examples of the carboxyl-activating reagent include N,N-dicyclohexylcarbodiimide, diethyl phosphorocyanidate, carbonyldiimidazole, 1-methyl-2-halopyridinium iodide and the like. Examples of the organic solvent include hydrocarbons such as hexane, benzene, toluene and the like, halogenated hydrocarbons such as chloroform, dichloromethane, 1,2-dichloroethane and the like, ethers such as diethyl ether, tetrahydrofuran, dioxane and the like, ethyl acetate, acetonitrile, dimethylformamide and the like.

The compound (III) may be converted into an acid halide using a halogenating agent such as phosphorus pentachloride, thionyl chloride, thionyl bromide or triphenyl phosphine dibromide or the like.

The reaction temperature for this reaction ranges from −10° to 120° C and the reaction time is about 1 to 5 hours.

When at least one of R₁, R₂ and R₃ in the compound (V) is a group that can be removed, such as an acyl group, a benzyl group (e.g., benzyl, p-methoxybenzyl, o-nitrobenzyl, p-nitorbenzyl, p-chlorobenzyl, p-bromobenzyl, p-cyanobenzyl, diphenylmethyl, etc.) or the like, optionally, the group may be removed.

Removal of the acyl group can be carried out by acid or base hydrolysis.

Any acid and base can be used without particular limitation. Examples of such an acid include hydrogen chloride, hydrogen bromide, hydrogen fluoride, sulfuric acid, fluorosulfuric acid, perchloric acid, phosphoric acid, boric acid, p-toluenesulfonic acid, trifluoromethanesulfonic acid, methanesulfonic acid, trifluoroacetic acid, trichloroacetic acid, acetic acid and H+ type ion exchange resin. These substances can be used as they are, or dissolved or suspended in water or an organic solvent as necessary. These acids can be used alone or in combination thereof.

Examples of the base include sodium hydroxide, potassium hydroxide, lithium hydroxide, sodium carbonate, potassium carbonate, lithium carbonate, sodium hydrogen carbonate, potassium hydrogen carbonate, lithium hydrogen carbonate, calcium hydroxide, barium hydroxide, ammonia and primary, secondary and tertiary amines.

Any reaction solvent can be used without particular limitation so long as it does not interfere with the reaction, but water and highly hydrophilic solvents are normally used, such as acetone, methyl ethyl ketone, methanol, ethanol, n-propanol, isopropanol, acetonitrile, propionitrile, tert-butanol, dioxane, tetrahydrofuran, ethyl ether, ethylene glycol dimethyl ether, diethylene glycol dimethyl ether, ethyl acetate, dimethylformamide, dimethylacetamide, dimethylsulfoxide and hexamethylphosphoramide. These solvents can be used alone or in combination thereof.

The reaction temperature ranges from −10° to 120° C. and the reaction time ranges from about 1 to 20 hours.

Removal of the benzyl group can normally be carried out by the reaction with a Lewis acid.

Examples of the Lewis acid include aluminum chloride, titanium tetrachloride, tin tetrachloride, boron trifluoride ether complex, boron tribromide, zinc chloride and the like.

Any reaction solvent can be used without particular limitation so long as it does not interfere with the reaction. Examples of the solvent include halogenated hydrocarbons such as chloroform, dichloromethane, 1,2-dichloroethane and the like, ethers such as diethyl ether, tetrahydrofuran, dioxane and the like, acetonitrile and the like.

The reaction temperature ranges from −10° to 120° C. and the reaction time is from about 5 hours to 2 days.

The compound having the amidated carboxyl group of

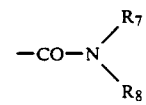

can be prepared by an amide synthetic reaction of saccharoascorbic acid according to the scheme 2:

Scheme 2

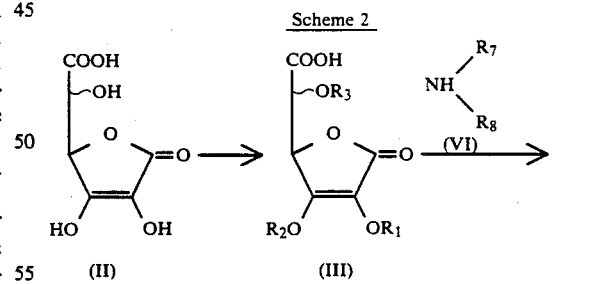

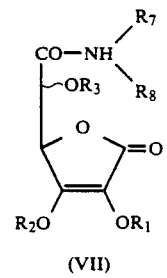

(VII)

wherein R₇ and R₈ are as defined above.

As seen from the scheme 2, the compound (VII) is obtained by the reaction of the compound (III) with ammonia or an amine represented by the formula (VI).

The production of the compound (III) from the compound (II) can be carried out as described above.

The production of the compound (VII) by the reaction of the compounds (III) and (VI) can be carried out by a known method of an amide synthetic reaction.

For example, the reaction can be carried out using a carboxyl-activating reagent in an organic solvent as described with respect to the thiol ester compound.

The compound (III) may be converted into an acid halide as described above and then, reacted with the compound (VI) in one of the above organic solvents in the presence of a base such as pyridine or triethylamine.

The reaction temperature for this reaction ranges from $-10°$ to $120°$ C and the reaction time is about 1 to 5 hours.

When at least one of $R_1$, $R_2$ and $R_3$ in the compound (VII) is a group that can be removed, such as the abovedescribed acyl group or benzyl group, optionally, such a group may be removed.

Removal of the acyl group can be carried out by acid or base hydrolysis as described above.

Removal of the benzyl group can normally be carried out by catalytic hydrogenation.

Examples of the catalyst include palladium, palladium chloride, platinum oxide, platinum black, ruthenium and the like. These may be supported on activated carbon, alumina, silica gel and the like.

Any reaction solvent can be used without particular limitation so long as it does not interfere with the reaction. Examples of the solvent include methanol, ethanol, propanol, ethyl acetate, acetic acid, acetonitrile, dioxane, tetrahydrofuran, ethyl ether, 1,2-dimethoxyethane, ethylene glycol dimethyl ether, chloroform, dichloromethane, benzene, toluene, water and the like. These solvents can be used alone or in combination thereof.

The reaction temperature ranges from $10°$ to $100°$ C. and the reaction time is from 1 to 10 hours. The reaction can be carried out under atmospheric pressure or higher pressure.

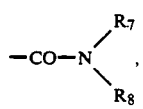

When $-COR_4$ of the formula (I) is

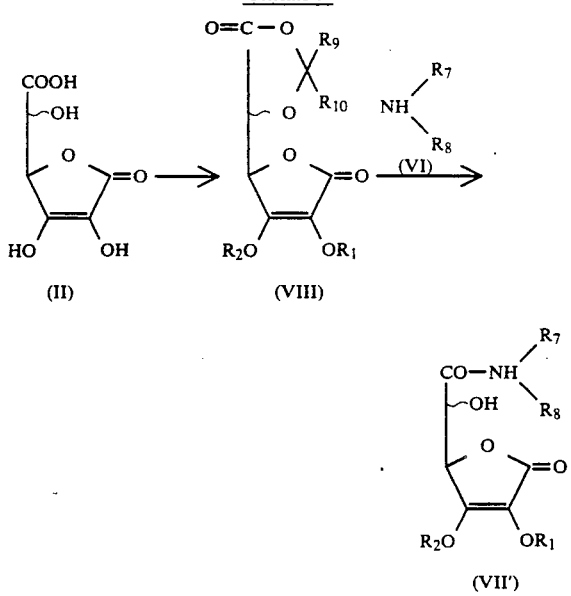

the compound (I) can also be produced according to the scheme 3:

wherein $R_1$, $R_2$, $R_7$ and $R_8$ are as defined above; and $R_9$ and $R_{10}$ are independently hydrogen, methyl, ethyl, phenyl or $R_9$ and $R_{10}$ are bonded to form $-(CH_2)_{4-5}-$.

As seen from the scheme 3, the compound (VII') is obtained by the reaction of the compound (VIII) with the compound (VI). When either of $R_1$ and $R_2$ represents a group that can be removed by reduction or by hydrolysis, it may optionally be removed as described above. The compound (VIII) can be obtained by a known method, for example, that disclosed in EP-A-0 295 842 or can be produced according to the methods as described in the scheme hereinafter.

The reaction of the compound (VIII) with the compound (VI) can be carried out by heating the reaction mixture in an organic solvent.

Examples of the solvent include hydrocarbons such as hexane, benzene toluene and the like, halogenated hydrocarbons such as chloroform, dichloromethane, 1,2-dichloroethane and the like, ethers such as diethyl ether, tetrahydrofuran, dioxane and the like, acetonitrile, dimethylformamide, dimethylsulfoxide and the like.

The reaction temperature ranges from $50°$ to $150°$ C. and the reaction time is from 5 to 20 hours.

When $-COR_4$ of the formula (I) is $-COOR_5$, the compound (I) can also be produced as follows.

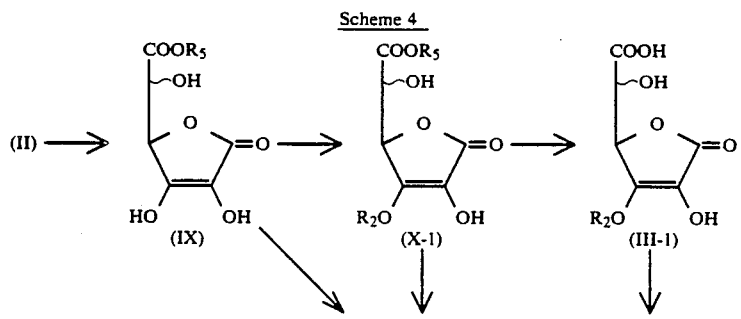

Scheme 4

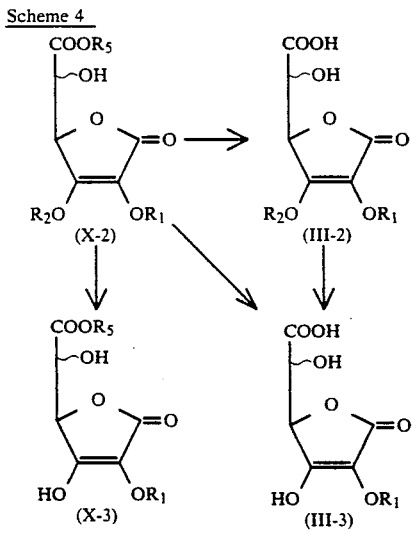

wherein $R_1$, $R_2$ and $R_5$ are as defined above.

The compound (IX) is obtained by a known method (EP-A-0 295 842). Further, the compounds (X-1)~(X-3) and (III-1)~(III-3) can be produced from the compounds (IX) as a starting material.

The compounds (X-1) are produced by the reaction of a compound (IX) with a compound represented by the formula $R_2X$ wherein $R_2$ is as defined above and X is halogen such as chlorine, bromine, iodine, etc., alkylsulfonyloxy such as methanesulfonyloxy, trifluoromethanesulfonyloxy, etc., arylsulfonyloxy such as benzenesulfonyloxy, p-toluenesulfonyloxy, etc., in the presence of an equivalent amount of a base.

Further, the compounds (X-1) are hydrolyzed by a conventional method to obtain the compounds (III-1). When $R_5$ of the compounds (X-1) is a group that can be removed by reduction, the compound (III-1) can be also obtained by reduction.

The compounds (X-2) are produced by the reaction of the compound (X-1) with a compound represented by the formula $R_1X$ wherein $R_1$ and X are as defined above, in the presence of an equivalent amount of a base.

In the case that both $R_1$ and $R_2$ are the same, the compound (X-1) can be produced from the compound (IX) by reacting the latter with two equivalent amounts of $R_1X$ in the presence of two equivalent amounts of a base.

Further, the compounds (X-2) are hydrolyzed by a conventional method to obtain the compound (III-2). When $R_5$ of the compound (X-2) is the group that can be removed by reduction, the compound (III-2) can be also obtained by reduction.

When $R_2$ of the compound (X-2) at the 3-position is the group that can be removed by reduction, the compound (X-3) can be produced from the compound (X-2) as a starting material. Also, the compound (III-3) can be produced from the compound (III-2) as a starting material.

Particularly, in the case where both of $R_2$ and $R_5$ are groups that can be removed by reduction or by hydrolysis, the compound (III-3) can be produced from the compound (X-2) by reduction or by hydrolysis in one step.

Examples of the groups that can be removed by reduction include benzyl, p-methoxybenzyl, o-nitrobenzyl, p-nitrobenzyl, p-chlorobenzyl, p-bromobenzyl, p-cyanobenzyl, diphenylmethyl and the like.

Examples of the groups that can be removed by hydrolysis include alkoxyalkyl group such as methoxymethyl, tert-butoxymethyl, 1-ethoxyethyl, 1-methyl-1-methoxyethyl and the like.

The etherifications described above are normally carried out under following conditions.

A base can be used for this reaction without any particular limitation. Examples of such bases include sodium hydride, calcium hydride, lithium hydride, lithium hydroxide, lithium hydrogen carbonate, lithium carbonate, sodium methoxide, sodium ethoxide, sodium hydroxide sodium hydrogen carbonate, sodium carbonate, potassium hydroxide, potassium hydrogen carbonate, potassium carbonate, magnesium hydroxide, magnesium carbonate, calcium hydroxide, barium hydroxide, barium carbonate, pyridine, tertiary amines, ammonium hydroxide having substituents

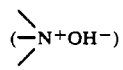

and the like.

A reaction solvent can be used without any particular limitation so long as it does not interfere with the reaction, but normally a polar solvent is used. Examples thereof include acetonitrile, propionitrile, benzonitrile, formamide, dimethyl formamide, dimethyl acetamide, dimethylsulfoxide, sulfolane, hexamethylphosphoramide, acetone, methylethylketone, dioxane, tetrahydrofuran, ethylene glycol dimethyl ether, diethylene glycol dimethyl ether, water and the like. These solvents can be used alone or in combination thereof.

The reaction temperature ranges from 0° to 100° C., preferably, 10 to 80° C. The reaction time depends upon reactants, reaction reagents, reaction conditions and the like. Normally, it ranges from 30 minutes to 4 days.

The hydrolysis of an ester at the 6-position and —$OR_2'$ at the 3-position can be normally carried out under acidic conditions.

Any acid can be used without any particular limitation.

Examples of acids include hydrogen chloride, hydrogen bromide, hydrogen iodide, hydrogen fluoride, sulfuric acid, fluorosulfuric acid, perchloric acid, phosphoric acid, boric acid, p-toluenesulfonic acid, trifluoromethanesulfonic acid, methanesulfonic acid, trifluoroacetic acid, trichloroacetic acid, acetic acid, $H^+$ type ion-exchange resin and the like. These substances may be used as they are, or dissolved or suspended in water or organic solvent as necessary. These acids can be used alone or in combination thereof.

A reaction solvent can be used without any particular limitation so long as it does not interfere with the reaction. Preferably, a hydrophilic solvent is normally used.

The reduction can be normally carried out by catalytic hydrogenation.

Examples of the catalyst include palladium, palladium chloride, platinum oxide, platinum black, ruthenium, etc. These may be supported on activated carbon, alumina, silica gel and the like.

A reaction solvent can be used without any limitation. Examples of the solvents include methanol, ethanol, propanol, ethyl acetate, acetic acid, acetonitrile, dioxane, tetrahydrofuran, ethyl ether, 1,2-dimethoxyethane, ethylene glycol dimethyl ether, chloroform, dichloromethane, benzene, toluene, water and so on. These solvents can be used alone or in combination thereof.

The reaction temperature ranges from 10° to 100° C. Reaction time is 1 to 10 hours. The reaction can be carried out under atmospheric pressure or higher pressure.

The other production method is shown in the scheme

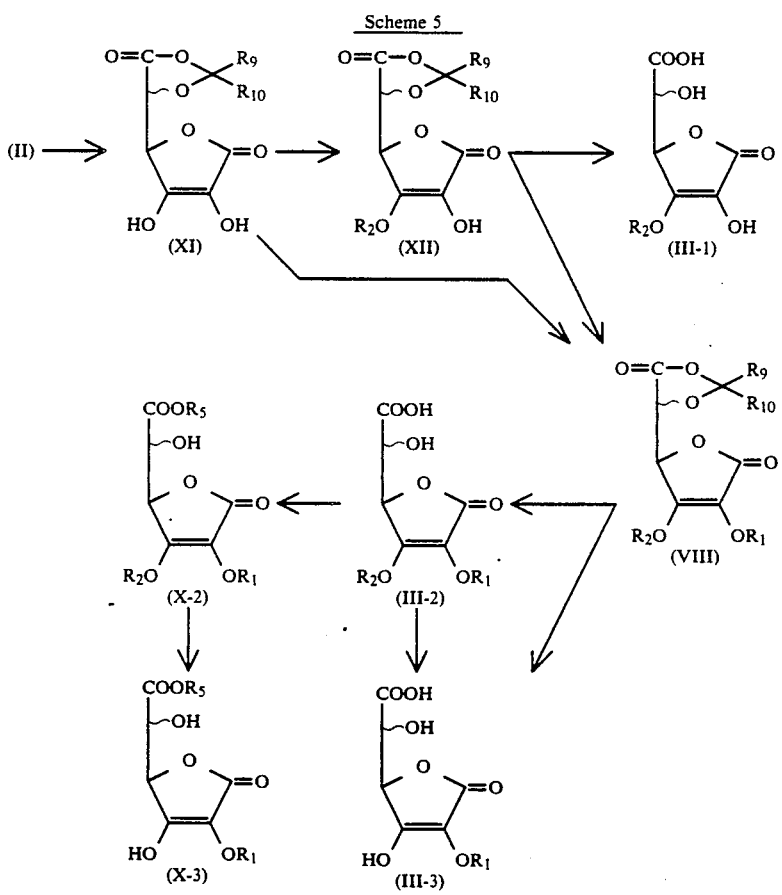

Examples of the solvent include acetone, methylethylketone, methanol, ethanol, n-propanol, isopropanol, acetonitrile, propionitrile, tert-butanol, dioxane, tetrahydrofuran, ethylether, ethylene glycol dimethyl ether, diethylene glycol dimethyl ether, ethyl acetate, dimethylformamide, dimethylacetamide, dimethylsulfoxide, hexamethylphosphoramide, water and the like. These solvents can be used alone or in combination thereof.

The reaction temperature ranges from 0 to 100° C., preferably 10 to 80° C. The reaction time depends upon reactants, reaction reagents, reaction conditions and the like. Normally, it ranges from 1 to 10 hours.

wherein $R_1$, $R_2$, $R_5$, $R_9$ and $R_{10}$ are as defined above.

As shown in the scheme 5, the compounds (X-2)∼(X-3) and (III-1) - (III-3) are produced from the compounds (XII). The compound (XI), which forms 4-oxo-1,2-dioxorane ring to protect at 5- and 6-position, can be obtained by a known method (EP-A-0 295 842).

The compounds (XII) are produced by the reaction of a compound represented by the formula.

$R_2X$ wherein $R_2$ and X are as defined above, with the compound (XI) in the presence of an equivalent amount of a base. The 4-oxo-1,3-dioxorane ring of a compound (XII) is subjected to hydrolysis to obtain a compound (III-1).

The compounds (VIII) (XIII) are produced by the reaction of a compound represented by the formula $$R_1X$$

wherein $R_1$ and X are as defined above, with the compound (XII) in the presence of an equivalent amount of a base.

In the case that both $R_1$ and $R_2$ are the same, the compound (VIII) (XIII) can be produced by reacting the compound (XI) with two equivalent amounts of $R_1X$ in the presence of two equivalent amounts of a base.

The compounds (VIII) (XIII) are subjected to hydrolysis to obtain the compound (III-2). The 6-carboxylic group of the obtained compound (III-2) is subjected to esterification to obtain the compound (X-2).

Particularly, in the case that $R_2$ of the compounds (III-2) or (X-2) can be removed by reduction, the compounds (III-3) and (X-3) are respectively produced from the compounds (III-2) and (X-2) by a conventional method. These production processes have been described as before.

In the case that $R_2$ of the compounds (VIII) is removed by hydrolysis, the compound (III-3) can be obtained by hydrolyzing the compound (VIII) in one step.

The process proceeding from the compounds (I) to (XI) is carried out by reaction of the compound (I) with a ketone or aldehyde such as formaldehyde, acetaldehyde, acetone, propionaldehyde, methylethylketone, diethylketone, cyclopentanone, cyclohexanone, benzaldehyde or the like in the presence of an acidic catalyst. Also, the compounds (XI) can be obtained by reacting the compound (I) with a ketal or an acetal, which is respectively produced from the ketone or aldehyde with a lower alkanol.

A reaction solvent can be used without particular any limitation so long as it does not interfere with the reaction. Examples of the solvent include acetonitrile, propionitrile, benzonitrile, nitromethane, nitroethane, nitrobenzene, dichloromethane, chloroform, tetrachloromethane, 1,1-dichloroethane, 1,2-dichloroethane, hexane, cyclohexane, benzene, toluene, xylene, dioxane, tetrahydrofuran, 1,2-dimethoxyethane, ethylene glycol dimethyl ether, diethyl carbonate, dimethylformamide, dimethylsulfoxide and the like. The ketone, aldehyde, ketal and acetal can be used as a solvent. These solvents can be used alone or in combination thereof.

Examples of acidic catalysts include a mineral acid such as hydrogen chloride, hydrogen bromide, hydrogen iodide, hydrogen fluoride, perchloric acid, sulfuric acid, fluorosulfuric acid, phosphoric acid, boric acid and the like, and organic acid such as p-toluenesulfonic acid, benzenesulfonic acid, methanesulfonic acid, trifluoromethanesulfonic acid, trifluoroacetic acid, H+type ion-exchange resin and the like, Lewis acids such as boron trifluoride, boron trichloride, boron tribromide, boron triiodide, aluminum chloride, titanium tetrachloride, zinc chloride, stannous chloride, stannic chloride and the like.

The reaction temperature ranges from 0° to 100° C. and the reaction time is from 1 to 24 hours.

In the etherification, the hydrolysis and the reduction, the same reaction conditions as before can be used.

The process proceeding from the compounds (III-2) to (X-2) can be carried out by a conventional esterification.

For example, (1) Direct esterification: reacting a compound (III-2) with an alcohol represented by the formula $$R_5OH$$

wherein $R_5$ is as defined above, in the presence of an acidic catalyst;

(2) reacting the compound (III-2) with a compound represented by the formula $$R_5X$$

wherein $R_5$ and X are as defined above, in the presence of a base;

(3) reacting the compound (III-2) with an alcohol represented by the formula $$R_5OH$$

wherein $R_5$ is as defined above, in the presence of a condensation reagent such as dicyclohexylcarbodiimide and the like;

(4) reacting the compound (III-2) with an olefinic compound such as isobutylene and the like in the presence of an acidic catalyst; and (5) reacting the compound (III-2) with an O-alkylating agent such as diazomethane, orthoformate and the like.

The derivatives of saccharoascorbic acid produced by the production method of the present invention can easily be isolated by conventional means such as extraction, chromatography (e.g., silica gel, polystyrene resin, activated charcoal, reverse phase, normal phase chromatography) or recrystallization from the residue obtained after distillation of low boiling point substances such as the solvent from the reaction product.

The pharmaceutical composition useful for preventing and treating thrombosis of the present invention can be prepared by admixing the saccharoascorbic acid derivative and a pharmaceutically acceptable carrier or diluent according to the conventional method and can be administered orally or parenterally.

The pharmaceutical composition of the present invention can be prepared in the form of tablets, capsules, powder, pellets, suppositories and the like. Further, the composition can be prepared in the form of injectable solution and suspension and the like.

The pharmaceutically acceptable carrier or diluent is not limited to a specific one and any suitable carrier or diluent can be used. Examples thereof include ethanol, sorbitol, mannitol, dextrose, maltose, glycerol, human serum albumin, sodium chloride and the like.

The pharmaceutical composition useful for preventing and treating thrombosis of the present invention can be administered in an amount sufficient for manifesting the desired prophylactic and therapeutic effects in the human body. The amount varies according to, for example, the age and body weight of a particular patient as well as a particular administration route, dosage form and the like.

For example, in the case of an adult patient, the pharmaceutical composition of the present invention can be administered orally or parenterally in a daily dosage of 0.1 to 20 mg/kg as the saccharoascorbic acid derivative and can be administered 1 to 6 times in a day.

Toxicity of the saccharoascorbic acid derivatives of the present invention is low.

The pharmaceutical composition containing the saccharoascorbic acid derivative of the present invention promotes and/or induces the production of plasminogen activator by vascular endothelial cells to accelerate fibrinolysis and, therefore, it can be used for preventing and treating thrombosis.

The following Preparations and Examples further illustrate the present invention in detail but are not to be construed to limit the scope of thereof.

Preparation 1

2,3-Di-0-benzyl-D-glucosaccharoascorbic acid n-octadecanethiolester

5-O-Acetyl-2,3-di-O-benzyl-D-glucosaccharoascorbic acid (4.89 g) prepared according to the method disclosed in EP-A-0 296 842 was dissolved in dichloromethane (30 ml). Phosphorus pentachloride (2.59 g) was added to the solution and the mixture was stirred at room temperature for 30 minutes. The mixture was distilled off under reduced pressure to remove low boiling point substances to obtain an acid chloride in the form of a paste.

The acid chloride was dissolved in dichloromethane (20 ml) and to the solution was added dropwise a solution of n-octadecyl mercaptan (3.40 g) in dichloromethane (5 ml) with ice-cooling.

Then, a mixture of triethylamine (1.20 g) and dichloromethane (3 ml) was slowly added dropwise and the resulting mixture was stirred for 4 hours.

The reaction mixture was poured into water (100 ml) and extracted 3 times with dichloromethane. After drying the extract, the solvent was distilled off and the residue was chromatographed on a silica gel column (solvent: ethyl acetate-hexane=1 : 5) to obtain crude crystals of 5-O-acetyl-2,3-di-0-benzyl-D-glucosaccharoascorbic acid n-octadecanethiolester (2.97 g).

Yield: 36.8%

Melting point: 61°-62° C. (recrystallized from hexane)

IR (KBr) cm$^{-1}$: 1770, 1750, 1685, 1670

$^1$H-NMR (CDCl$_3$)δ: 0.88 (t, 3H), 1.10-1.60 (m, 32H), 2.16 (s, 3H), 2.74 (t, 2H), 5.09 (s, 2H), 5.11 (d, 1H), 5.20 (s, 2H), 5.72 (d, 1H, J=3Hz), 7.13-7.38 (m, 10H)

MS: m/e 680 (M), 620, 588

Elemental analysis (%),

Calcd for C$_{40}$H$_{56}$O$_7$S: C, 70.55; H, 8.29.

Found C, 70.47; H, 8.27.

5-O-Acetyl-2,3-Di-0-benzyl-D-glucosaccharoascorbic acid n-octadecanethiolester (2.97 g) thus prepared was dissolved in a mixture of 2 N sulfuric acid (20 ml) and acetonitrile (100 ml) and the solution was heated under reflux for 20 hours. After the completion of the reaction, acetonitrile was distilled off, water (50 ml) was added to the residue and the mixture was extracted 3 times with dichloromethane.

After drying the extract, the solvent was distilled off and the residue was chromatographed on a silica gel column (solvent: ethyl acetate-hexane=1 : 5) to obtain 2,3-di-O-benzyl-D-glucosaccharoascorbic acid n-octadecanethiolester (2.67 g).

Yield: 95.8%

Melting point: 55°-56° C. (recrystallized from hexane)

IR (KBr) cm$^{-1}$: 3600-3300, 1770, 1670

$^1$H-NMR (CDCl$_3$)δ: 0.88 (t, 3H), 1.08-1.53 (m, 32H), 2.68 (m, 2H), 4.67 (d, 1H, J=2Hz), 5.00-5.17 (m, 5H), 7.09-7.38 (m, 10H), Figuring for OH was difficult because their band was very broad.

MS: m/e 638 (M), 570, 546

Elemental analysis (%),

Calcd for C$_{38}$H$_{54}$O$_6$S: C, 71.44; H, 8.52.

Found: C, 71.45; H, 8.56.

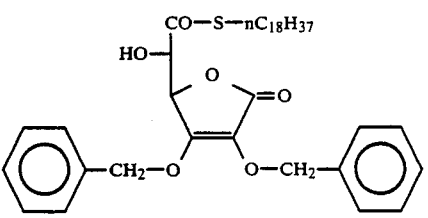

Preparation 2

5-O-Acetyl-2,3-di-0-benzyl-D-glucosaccharoascorbic acid n-octadecylamide

5-O-Acetyl-2,3-Di-0-benzyl-D-glucosaccharoascorbic acid (5.00 g) was dissolved in dichloromethane (40 ml). Phosphorus pentachloride (2.77 g) was added to the solution and the mixture was stirred at room temperature for 30 minutes.

The mixture was distilled off under reduced pressure to remove low boiling point substances to obtain an acid chloride in the form of a paste. The acid chloride was dissolved in dichloromethane (30 ml) and to the solution was added dropwise a solution of n-octadecylamine (3.40 g), triethylamine (1.20 g) and dichloromethane (150 ml) with ice-cooling. The mixture was stirred for one hour. The reaction mixture was poured into water (200 ml) and extracted 3 times with dichloromethane. The extract was dried over sodium sulfate and the solvent was distilled off. The residue was chromatographed on a silica gel column (solvent: ethyl acetate-hexane=1 : 1) to obtain 5-O-acetyl-2,3-di-O-benzyl-D-glucosaccharoascorbic acid noctadecylamide (6.10 g)

Yield: 75.8%

Melting point: 51°-53° C. (recrystallized from dichloromethane-hexane=1 : 4)

IR (KBr) cm$^{-1}$: 3320, 1790, 1750, 1690, 1670

$^1$H-NMR (DMSO-d$_6$)δ: 0.85 (t, 3H), 1.10-1.40 (m, H), 2.10 (s, 3H), 2.90-3.15 (m, 2H), 4.94 (s, 2H), 5.18-5.40 (m, 4H), 7.25-7.42 (m, 10H), 8.00 (br, NH)

Elemental analysis (%),

Calcd for C$_{40}$H$_{57}$NO$_7$: C, 72.37; H, 8.65; N, 2.11.

Found: C, 72.49; H, 8.87; N, 2.15.

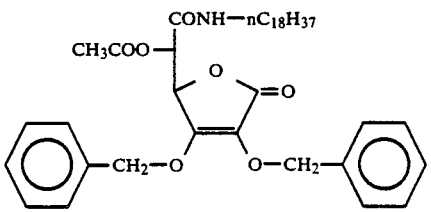

Preparation 3

2,3-Di-O-benzyl-D-glucosaccharoascorbic acid n-octadecylamide

5-O-Acetyl-2,3-di-O-benzyl-D-glucosaccharoascorbic acid n-octadecylamide (5.90 g) prepared in Preparation 2 was dissolved in a mixture of 2 N sulfuric acid (20 ml) and acetonitrile (60 ml), and heated under reflux for 12 hours.

After completion of the reaction, acetonitrile was distilled off and water (200 ml) was added to the residue. The mixture was extracted 3 times with dichloromethane.

After drying the extract over sodium sulfate, the solvent was distilled off. The residue was chromatographed on a silica gel column (solvent: ethyl acetate-hexane = 1 : 1) to obtain 2,3-di-O-benzyl-D-glucosaccharoascorbic acid n-octadecylamide (3.50 g).

Yield: 63.3%

Melting point: 105°–107° C.

IR (KBr) cm$^{-1}$: 3500–3200, 1755, 1675, 1645

$^1$H-NMR (DMSO-d$_6$) δ: 0.85 (t, 3H), 1.04–1.28 (m, 32H), 2.83–3.03 (m, 2H), 4.30 (m, 1H), 4.95 (s, 2H), 5.10–5.20 (m, 3H), 6.37 (d, OH), 7.18–7.42 (m, 10H), 7.66 (br, NH)

Elemental analysis (%),

Calcd for C$_{38}$H$_{55}$NO$_6$: C, 73.40; H, 8.91; N, 2.25.

Found: C, 73.62; H, 8.93; N, 2.22.

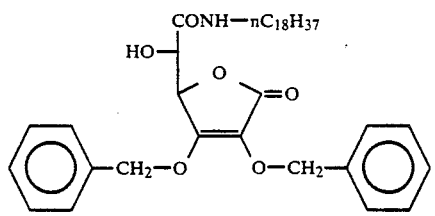

Preparation 4

3-O-Benzyl-D-glucosaccharoascorbic acid methyl ester

D-Glucosaccharoascorbic acid methyl ester monohydrate (22.2 g) was dissolved in dimethylsulfoxide (200 ml). To this solution was added potassium carbonate (6.9 g) and then benzyl chloride (12.7 g), followed by stirring at about 60° C. for 4 hours. Then, the reaction mixture was diluted with water (500 ml) and extracted with ethyl acetate (1 liter). After washing with water, the extract was dried over anhydrous magnesium sulfate. The solvent was distilled off under reduced pressure and the residue was chromatographed on a silica gel column (solvent: ethyl acetate) to obtain 3-O-benzyl-D-glucosaccharoascorbic acid methyl ester as a oily substance (21.0 g).

Yield 71.0%

IR (liq. film) cm$^{-1}$: 3350, 1750, 1690

$^1$H-NMR (CDCl$_3$) δ: 3,64 (s, 3H), 3.8–4.3 (br. 2H), 4.66 (d, 1H), 5.06 (d, 1), 5.45 (s, 2H), 7.37 (s, 5H)

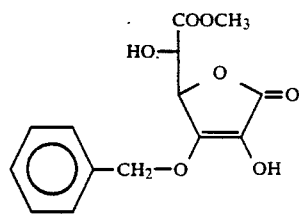

Preparation 5

3-O-Benzyl-L-gulosaccharoascorbic acid methyl ester

A mixture of L-gulosaccharoascorbic acid monohydrate (196 g), concentrate HCl (5 ml) and methanol (800 ml) was refluxed with heating for 4 hours. Then, the mixture was evaporated under reduced pressure to obtain crude L-gulosaccharoascorbic acid methyl ester in the form of a viscous liquid. This crude reaction product was dissolved in dimethylsulfoxide (800 ml). To this solution were added potassium carbonate (276 g) and benzyl chloride (242 g), followed by stirring at room temperature for 16 hours. Then, the reaction mixture was diluted with water (500 ml) and then extracted 3 times with dichloromethane (in total, about 3 liters of dichloromethane was used). After drying over anhydrous sodium sulfate, the solvent was distilled off under reduced pressure and the residue was fractionally purified by silica gel column chromatography (solvent: dichloromethane) to obtain 3-O-benzyl-L-gulosaccharoascorbic acid methyl ester (48.7 g) as an oily substance together with 2,3-di-O-benzyl-L-gulosaccharoascorbic acid methyl ester (142 g).

Yield: 17.6%

IR (liq. film) cm$^{-1}$: 3600–3100, 3050, 1760, 1690

$^1$H-NMR (CDCl$_3$) δ: 2.94 (d, 1H), 3.87 (s, 3H), 4.50 (m, 1H), 4.88 (br. 1H), 4.99 (d, 1H), 5.38–5.55 (q, 2H), 7.2–7.45 (m, 5H)

Elemental analysis (%),

Calcd C$_{14}$H$_{14}$O$_7$: C, 57.14; H, 4.80.

Found: C, 56.87; H, 4.53.

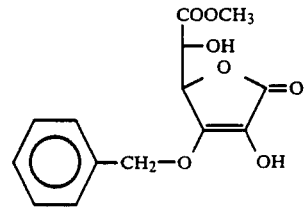

Preparation 6

3-O-Octadecyl-D-glucosaccharoascorbic acid n-octadecyl ester

D-Glucosaccharoascorbic acid n-octadecyl ester (5.0 g) was dissolved in dimethylsulfoxide (30 ml). To this solution were added potassium carbonate (1.25 g) and then a solution of n-octadecyl iodide (4.30 g) in tetrahydrofuran (15 ml), followed by heating at 60° C. for 6 hours. Then, the reaction mixture was diluted with water (400 ml) and adjusted to pH 3 with dil. HCl and extracted twice with ethyl ether. The extract was dried and evaporated under reduced pressure. The residue was chromatographed on a silica gel column (solvent: ethyl acetate-hexane=1 : 2) and the resulting product was recrystallized from dichloromethane-hexane (1 : 4) to obtain 3-O-octadecyl-D-glucosaccharoascorbic acid n-octadecyl ester 0.5 hydrate (2.23 g).

Yield: 28.0%

Melting point: 60°-67° C.

IR (KBr) cm$^{-1}$: 3650-3000, 1765, 1740, 1700

$^1$H-NMR (CDCl$_3$) δ: 0.88 (m, 6H), 1.18-1.75 (m, 64H), 4.19 (t, 2H, J=7Hz), 4.39 (t, 2H, J=6Hz), 4.57 (d, 1H, J=2Hz), 4.97 (d, 1H, J=2Hz), Figuring for OH was difficult because its band was very broad.

Elemental analysis (%),

Calcd C$_{42}$H$_{78}$O$_7$·0.5H$_2$O: C, 71.65; H, 11.45.

Found: C, 71.53; H, 11.63.

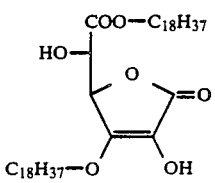

Preparation 7

2,3-Di-O-benzyl-D-glucosaccharoascorbic acid benzenethiolester

5-O-Acetyl-2,3-di-O-benzyl-D-glucosaccharoascorbic acid (1.00 g) was dissolved in 20 ml of dry dichloromethane. To this solution was added 1.06 g of triphenylphosphine dibromide, followed by stirring at room temperature for 5 minutes. Then, 0.27 g of thiophenol was added, followed by stirring for 10 minutes. To this mixture, 0.19 g of pyridine was added dropwise, followed by stirring at room temperature for 3 hours.

The reaction mixture was poured into 100 ml of water and thrice extracted with dichloromethane. The extract was dried over sodium sulfate.

After the solvent was distilled off, the residue was subjected to silica gel column chromatography (solvent: ethyl acetate-hexane=1:4) to yield 0.82 g of pasty 5-O-Acetyl-2,3-di-O-benzyl-D-glucosaccharoascorbic acid benzenethiolester.

Yield: 67.2 %

IR (liq. film) cm$^{-1}$: 1760, 1680

$^1$H-NMR (CDCl$_3$) δ: 2.23 (s, 3H), 5.12 (s, 2H), 5.15 (d, 1), 5.20 (s, 2H), 5.84 (d, 1H, J=3Hz), 7.00-7.41 (m, 15H)

Elemental analysis (%),

Calcd for C$_{28}$H$_{24}$O$_7$S: C, 66.65; H, 4.79.

Found: C, 66.63; H, 4.84.

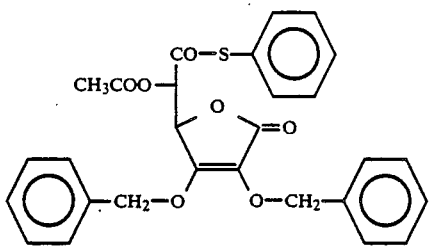

5-O-Acetyl-2,3-di-O-benzyl-D-glucosaccharoascorbic acid benzenethiolester (0.71 g) was dissolved in a mixture of 2 N sulfuric acid (4 ml) and acetonitrile (20 ml). This solution was refluxed with heating for 6 hours.

After the completion of the reaction, the acetonitrile was distilled off. The resulting residue was diluted with water (50 ml) and extracted 3 times with dichloromethane. After drying the extract with sodium sulfide, the solvent was distilled off. The resulting residue was chromatographed on a silica gel column (solvent: ethyl acetate-hexane=1 : 3) and the resulting product was recrystallized from dichloromethanehexane (1 : 5) to obtain 2,3-di-O-benzyl-D-glucosaccharoascorbic acid benzenethiolester (0.51 g).

Yield: 78.2%

Melting point: 116°-118° C.

IR (KBr) cm$^{-1}$: 3600-3200, 1770, 1680

$^1$H-NMR (CDCl$_3$) δ: 3.82 (d, OH, J=7Hz), 4.82 (dd, 1H, J=7.2Hz), 5.05-5.20 (m, 5H), 6.88-7.45 (m, 15H)

Elemental analysis (%),

Calcd for C$_{26}$H$_{22}$O$_6$S: C, 67.52; H, 4.79.

Found: C, 67.52; H, 4.81.

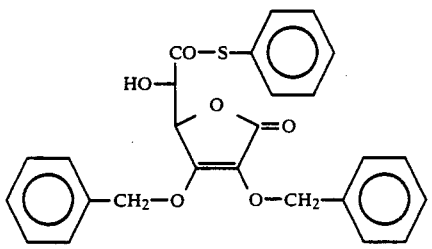

Preparation 8

2,3-Di-O-benzyl-D-glucosaccharoascorbic acid N,N-pentamethyleneamide

5-O-Acetyl-2,3-di-O-benzyl-D-glucosaccharoascorbic acid (5.80 g) was dissolved in dichloromethane (40 ml). To this solution was added phosphorus pentachloride (3.22 g), followed by stirring at room temperature for 30 minutes. Low boiling point substances were distilled off under reduced pressure to obtain an acid chloride in the form of a paste. This acid chloride was dissolved in dichloromethane (30 ml). To this solution was added dropwise a mixed solution of piperidine (1.26 g), triethylamine (1.50 g) and dichloromethane (6 ml) with ice-cooling, followed by stirring at room temperature for 1 hour. The reaction mixture was poured into water (80 ml) and extracted 3 times with dichloromethane. The extract was dried over sodium sulfate. After the solvent was distilled off, the residue was chromatographed on a silica gel column (solvent: ethyl acetate-hexane=1 : 1) to obtain 5-O-acetyl-2,3-di-O-benzyl-D-glucosaccharoascorbic acid N,N-pentamethyleneamide (5.28 g).

5-O-Acetyl-2,3-di-O-benzyl-D-glucosaccharoascorbic acid N,N-pentamethyleneamide (3.70 g) was dissolved in a mixture of 2 N sulfuric acid (20 ml) and acetonitrile (60 ml) and the solution was refluxed with heating for 8 hours. The acetonitrile was distilled off and the residue was diluted with water (50 ml) and extracted 3 times with dichloromethane. After drying the extract over sodium sulfate, the solvent was distilled off and the residue was chromatographed on a silica gel column (solvent: ethyl acetate-hexane=1 : 1) to obtain crude crystals of 2,3-di-benzyl-D-glucosaccharoascorbic acid N,N-pentamethyleneamide (3.19 g).

Yield: 94.5%

Melting point: 101-104° C. (from dichloromethanehexane)

IR (KBr) cm$^{-1}$: 3450-3300, 1770, 1680, 1645

$^1$H-NMR (CDCl$_3$) δ: 1.40-1.70 (m, 6H), 3.20-3.53 (m, 4H), 3.80-4.20 (br., OH), 4.66 (s, 2H), 4.91 (d, 1H, J=11z), 5.15 (s, 2H), 5.18 (d, 1H, J=11z), 7.16-7.43 (m, 10 H)

MS: m/e 437 (M), 419, 346, 328

Elemental analysis (%),

Calcd for C$_{25}$H$_{27}$NO$_6$: C, 68.64; H, 6.22; N, 3.20.
Found: C, 68.51; H, 6 00; N, 3.14.

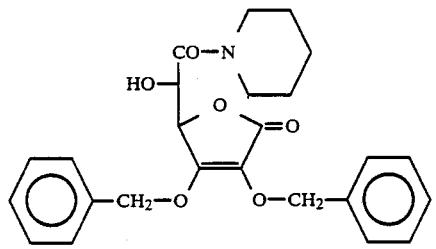

Preparation 9

2,3-Di-O-benzyl-D-glucosaccharoascorbic acid n-decylamide

5-O-Acetyl-2,3-di-O-benzyl-D-glucosaccharoascorbic acid (9.14 g) was dissolved in dichloromethane (60 ml). To this solution was added phosphorus pentachloride (5.08 g), followed by stirring at room temperature for 1 hour. Low boiling point substances were distilled off under reduced pressure to obtain an acid chloride in the form of a paste. This acid chloride was dissolved in dichloromethane (40 ml). To this solution was added dropwise a mixed solution of n-decylamine (3.67 g), triethylamine (2.36 g) and dichloromethane (10 ml) with ice-cooling, followed by stirring for 1 hour. The reaction mixture was poured into water (100 ml) and extracted 3 times with dichloromethane. The extract was dried over sodium sulfate. After the solvent was distilled off, the residue was chromatographed on a silica gel column (solvent: ethyl acetate-hexane=1 : 2) to obtain a paste of 5-O-acetyl-2,3-di-O-benzyl-D-glucosaccharoascorbic acid n-decylamide (11.32 g).

5-O-Acetyl-2,3-di-O-benzyl-D-glucosaccharoascorbic acid n-decylamide (10. 92 g) was dissolved in a mixture of 2 N sulfuric acid (30 ml) and acetonitrile (90 ml) and the solution was heated under reflux for 10 hours. Then, the acetonitrile was distilled off. The residue was diluted with water (80 ml) and extracted 3 times with dichloromethane. After drying the extract over sodium sulfate, the solvent was distilled off and the residue was chromatographed on a silica gel column (solvent: ethyl acetate-hexane=1 : 1) to obtain 2,3-di-O-benzyl-D-glucosaccharoascorbic acid n-decylamide (7.16 g).

Yield: 71.0%

Melting point: 130°-132° C. (recrystallized from dichloromethanehexane=1 : 1)

IR (KBr) cm$^{-1}$: 3400-3250, 1760, 1680, 1650

$^1$H-NMR (CDCl$_3$) δ0.88 (t, 3H), 1.10-1.38 (m, 16H), 2.64-3.26 (m, 2H), 4.33 (br., OH), 4.62 (dd, 1, J=5, 2Hz), 5.05 (s, 2H), 5.15 (s, 2H), 5.28 (d, 1, J=2Hz), 6.67 (t, NH), 7.10-7.40 (m, 10H)

MS: m/e 509 (M), 481

Elementary analysis (%),

Calcd for C$_{30}$H$_{39}$NO$_6$ C, 70.70; H, 7.71; N, 2.75.
Found: C, 70.64; H, 7.65; N, 2.70.

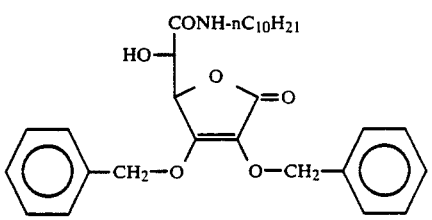

Preparation 10

2,3-Di-O-benzyl-D-glucosaccharoascorbic acid amide

5-O-acetyl-2,3-di-O-benzyl-d-glucosaccharoascorbic acid (5.0 g) was dissolved in dichloromethane (40 ml). To this solution was added phosphorus pentachloride (2.77 g), followed by stirring at room temperature for 30 minutes. Low boiling point substances were distilled off under reduced pressure to obtain an acid chloride in the form of a paste. This acid chloride was dissolved in dichloromethane (30 ml). To this solution was added dropwise a mixed solution of 3% (w/w) ammonia-dichloromethane (7.3 ml), triethylamine (1.21 g) and dichloromethane (50 ml) with ice-cooling, followed by stirring for 1 hour. The reaction mixture was poured into water (150 ml) and extracted 3 times with dichloromethane. The extract was dried over sodium sulfate. After the solvent was distilled off, the residue was chromatographed on a silica gel column (solvent: ethyl acetate-hexane=1 : 1) to obtain 5-O-acetyl-2,3-di-O-benzyl-D-glucosaccharoascorbic acid amide (3.50 g). Melting point: 140°-142° C.

This amide (3.0 g) was dissolved in a mixture of 2N sulfuric acid (20 ml) and acetonitrile (60 ml) and the solution was refluxed with heating for 12 hours. Then, the acetonitrile was distilled off. The residue was diluted with water (150 ml) and extracted 3 times with dichloromethane. After drying the extract over sodium sulfate, the solvent was distilled off and the residue was chromatographed on a silica gel column (solvent: ethyl acetate) to obtain 2,3-di-O-benzyl-D-glucosaccharoascorbic acid amide (2.10 g).

Yield: 78.1%

Melting point: 160°-163° C.

IR (KBr) cm$^{-1}$: 3600-3100, 1780, 1760, 1680, 1650

$^1$H-NMR (DMSO-d$_6$) δ: 4.30 (dd, 1H, J=6.2Hz), 4.95 (s, 2H), 5.10-5.26 (m, 3H), 6.29 (d, OH, J=6Hz), 7.18-7.50 (m, 10H), 7.68 (br., NH2)

Elemental analysis (%),

Calcd for C$_{20}$H19NO$_6$: C, 65.03; H, 5.18; N, 3.79.
Found: C, 65.10; H, 5.23; N, 3.75.

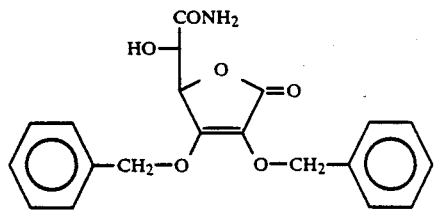

Example 1

Determination of capability of induction of plasminogen production by using vascular endothelial cells Activities of saccharoascorbic acid derivatives for the induction of plasminogen activator production by cultivated bovine lung aorta endothelial cells were determined by using plasminogen-containing fibrin plate method.

(1) Materials

(a) Bovine lung aorta endothelial cells

Bovine lung aorta endothelial cells CCL 209 purchased from American Type Culture Collection were used.

(b) Culture medium

Dulbecco's modified minimum essential medium containing 10% inactivated bovine fetal serum, penicillin G (100 U/ml) and streptomycin (100 μg/ml) was used.

(c) Fibrinogen solution

Bovine fibrinogen containing 75% clottable protein (manufactured by Seikagaku Kogyo Co., Ltd., Japan) was dissolved in phosphate buffer (50 mM, pH 7.4) and the solution was applied on a lysine Sepharose column. The fraction passed through the column was collected to obtain a fibrinogen free from both plasmin and plasminogen. The fibrinogen fraction thus obtained was diluted with phosphate buffer and the fiblinogen concentration was adjusted to make 10 mg/ml.

(d) Thrombin solution

Bovine thrombin (1000 units/vial, manufactured by Mochida Seiyaku Co., Ltd., Japan) was dissolved in physiological saline so that the concentration thereof became 10 units/ml.

(e) Plasminogen solution

Human plasminogen (51.5 units/vial, Nihon Pharmaceutical Co., Ltd., Japan) was dissolved in physiological saline so that the concentration thereof became 10 units/ml.

(f) Agarose solution

Agarose (Seakem ME manufactured by FMC Corporation, U.S.A.) was dissolved in Tris-HCl buffer (50 mM, pH 7.5)-12 mM NaCl so that the concentration thereof became 1% (W/V).

(g) Gel bond film

Gel bond film for agarose (manufactured by FMC Corporation, U.S.A.) cut into a rectangle (8.0 cm × 12.5 cm)

(h) Authentic human urokinase solution

Human urokinase (protein content: 0.88 mg/ml, manufactured by Nihon Pharmaceutical Co., Ltd., Japan) was diluted with Tris-HCl buffer (50 mM, pH 7.5)-12 mM NaCl containing 0.1% bovine serum albumin to prepare solutions having the urokinase concentrations of 50, 25, 12.5, 6.25 and 3.125 ng/ml, respectively.

(2) Determination

(a) Method for cultivation of bovine lung aorta endothelial cells and induction of plasminogen activator production by addition of saccharoascorbic acid derivatives A suspension of bovine lung aorta endothelial cells (number of subcultures: 21 to 26) was placed in each well of a plate having 96 wells (manufactured by A/S Nunc, Roskilde, Denmark) in an amount of 3,000 cells/100 μl/well and cultivated in an incubator containing 5% $CO_2$/95% air at 37° C. for 3 days to grow the cells in a pre-confluent state. After removing the culture medium, the cells were washed with PBS (−) and, again, 95 μl/well of the fresh culture medium was added.

A saccharoascorbic acid derivative was dissolved in dimethylsulfoxide (DMSO) in a concentration of 10 mM. The solution was diluted 10, 100 and 1000 times with the culture medium to obtain 1, 0.1 and 0.01 mM solutions, respectively. As the controls, DMSO was diluted 10, 100 and times with the culture medium. The diluted saccharoascorbic acid derivative and the controls were added to the 96-well plate in an amount of 5 μl/well so that the final concentrations became 50, 5 and 0.5 μM, respectively. The plate was incubated for 2 days. After incubation, the supernatant of the culture was collected and used as the sample for determination of plasminogen activator activity.

(b) Preparation of fibrin plate containing plasminogen and determination of plasminogen activator activity To the solution of bovine fibrinogen solution (10 ml) was added the human plasminogen solution (0.5 ml) and the mixture was maintained at 50° C. for 2 minutes. Then, the mixture was admixed with the agarose solution which had been dissolved with heating and maintained at 50° C. Immediately, the bovine thrombin solution (0.1 ml) was added, and the whole mixture was cast on the gel bond film and allowed to stand at room temperature for 1 hour to obtain a fibrin plate.

Holes of 3 mm in diameter were provided on the plate and the sample (5 μl) and the authentic human urokinase solution (5 μl) were added thereto. After the reaction at 37° C. for 6 hours, the diameter of the resulting lysis spot was measured and plasminogen activator activity of the sample was determined from a calibration curve.

(3) Results

The capabilities of induction of the plasminogen activator production by the saccharoascorbic acid derivatives obtained in Preparations 1, 2 and 3 are shown in Table 1.

TABLE 1

| Compounds | Concentration (μM) | Plasminogen activator activity (ng/ml) |
|---|---|---|
| Preparation 1 | 50 | 19.0 |
| | 5 | 13.5 |
| | 0.5 | 7.5 |
| Preparation 2 | 50 | 5.9 |
| | 5 | 16.0 |
| | 0.5 | 9.4 |
| Preparation 3 | 50 | 19.0 |
| | 5 | 12.0 |
| | 0.5 | 10.3 |
| Control | — | 3.8 |

As seen from Table 1, plasminogen activator activities are increased, at most, 5.0 times by the addition of the saccharoascorbic acid derivatives.

When the compounds obtained in the above Preparations 4 to 10 as well as following compounds disclosed in EP-A-0 295 845 were tested for the induction of plasminogen activator production according to the same manner as described above, the capabilities of induction of the production of plasminogen activator were also observed.

2,3-Di-O-benzyl-D-glucosaccharoascorbic acid methyl ester (EP-A-0 295 845, Reference Example 20)

2,3-Di-O-benzyl-D-glucosaccharoascorbic acid t-butyl ester (EP-A-0 295 845, Reference Example 29)

2,3-Di-O-benzyl-D-glucosaccharoascorbic acid n-octadecyl ester (EP-A-0 295 845, Reference Example 34)

Example 2

Enhancement of plasmin activity by intravenous administration to rats

A saccharoascorbic acid derivative was administered to rats intravenously. Blood was collected with time to prepare euglobulin fractions and their plasmin activities were determined. Plasmin activity was determined by the activity to hydrolyze S-2251 (H-D-Val-Leu-Lys-pNA manufactured by AB Kabi, Sweden).

(1) Materials (a) Animals

Male Sprague-Dawley rats (10–12 week old, body weight: 300–380 g; CLEA Japan Inc., Japan) were used. were used.

(b) S-2251 solution 3 mM solution of S-2251 (AB Kabi, Sweden) in distilled water was used.

(2) Administration method

A sample was suspended and dissolved in physiological saline containing 25% ethanol in an amount of 1 and 2 mg/ml. Then, 0.5 ml of each solution was administered intravenously to a rat anesthetized with ether.

(3) Determination of plasmin activity (a) Preparation of a euglobulin fraction

To blood (9 parts by volume) collected was added 3.8% sodium citrate solution (1 part by volume) and the mixture was centrifuged at 3,000 r.p.m. for 10 minutes. The resulting supernatant (0.5 ml) was adjusted to pH 5.2 by adding cold 0.017% acetic acid solution (9.5 ml) and the mixture was allowed to stand at 4° C. for 30 minutes. The precipitate was collected by centrifugation and dissolved in 0.05 M Tris-HCl buffer (pH 7.5)-0.012 M NaCl (0.5 ml) to obtain a euglobulin solution.

(b) Determination of activity for hydrolyzing S-2251

To the euglobulin solution (0.25 ml) were added 0.05 M Tris-HCl buffer (pH 7.5)-0.012 M NaCl (0.23 ml) and the S-2251 solution (0.02 ml) and the mixture was incubated at 37° C. for 30 minutes. Then, 50% acetic acid solution (0.05 ml) was added to the reaction mixture to terminate the reaction and the absorbance at the wavelength of 405 nm was measured.

According to the above method, the compound obtained in Preparation 1 was administered intravenously to rats (3 rats/group) at doses of 1 mg and 0.5 mg/rat, and plasmin activity in blood was determined with time. The results are shown in Table 2.

TABLE 2

| | Blood collection time (min) | Plasmin activity in blood ($\Delta A_{405} \times 10^3$/min) |
| --- | --- | --- |
| Administration group | 10 | 7.0 |
| | 30 | 6.0 |
| | 60 | 4.2 |

TABLE 2-continued

| | Blood collection time (min) | Plasmin activity in blood ($\Delta A_{405} \times 10^3$/min) |
| --- | --- | --- |
| (1 mg) | 240 | 2.6 |
| Administration group | 10 | 6.1 |
| | 30 | 5.0 |
| | 60 | 3.4 |
| (0.5 mg) | 240 | 2.0 |
| Control group | 10 | 2.3 |
| | 30 | 2.4 |
| | 60 | 2.0 |
| | 240 | 1.6 |

As seen from Table 2, plasmin activities in blood were remarkably increased in the administration groups and reached to, at highest, 3 times as high as that of the control group.

EXAMPLE 3

Enhancement of plasmin activity by oral administration to rats

The compound obtained in Preparation 1 was suspended in 5% gum arabic-physiological saline and administered orally to rats at a dose of 50 mg/rat. Then, plasmin activity in blood was measured with time. The results are shown in Table 3.

TABLE 3

| | Blood collection time | Plasmin activity in blood ($\Delta A_{405} \times 10^3$/min) |
| --- | --- | --- |
| Administration group (50 mg) | 10 min | 16.6 |
| | 30 min | 12.1 |
| | 1 hr | 9.7 |
| | 4 hr | 5.4 |
| | 24 hr | 2.3 |
| Control group | 10 min | 3.9 |
| | 30 min | 3.4 |
| | 1 hr | 3.4 |
| | 4 hr | 3.7 |
| | 24 hr | 1.9 |

As seen from Table 3, plasmin activities in blood of the administration group are 1.2 to 4.3 times as high as those of the control group.

EXAMPLE 4

Enhancement of plasmin activity by intravenous administration to rabbits

A saccharoascorbic acid derivative was administrated intravenously to rabbits. Blood was collected with time to prepare euglobulin fractions and their plasmin activities were determined by the activity to hydrolyze S-2251 (AB Kabi, Sweden).

(1) Materials (a) Animals

Male rabbits (Japan White, body weight: 3.0–3.5 kg, Rabiton Farm) were used.

(b) S-2251 solution

The S-2251 solution prepared according to the same manner as that described in Example 2 was used.

(2) Administration method

A sample was suspended and dissolved in physiological saline containing 25% ethanol in an amount of 2 or 6 mg/ml. Then, the solutions were administered to rabbits anesthetized with urethane and sodium pentobarbital (0.5 mg/kg and 90 mg/kg i.p., respectively) intravenously at doses of 3 and 10 mg/kg.

(3) Determination of plasmin activity

Plasmin activity was determined according to the same manner as that described in Example 2.

(4) Determination of clot lysis time

The euglobulin solution (0.2 ml) obtained according to the same manner as that described in Example 2 was placed in a small glass test tube (inner diameter: 0.5 cm, length: 5 cm) and 50 units thrombin solution (0.01 ml) was added to the test tube. The time required for lysing the coagulation caused was measured by a Euglobulin Lysis Analyzer (manufactured by Mebanix Corp., Japan).

The compound obtained by Preparation 1 was administered intravenously to rabbits (3 rabbits/group) and plasmin activity in blood was determined with time. The average values of the results are shown in Table 4.

TABLE 4

| | Blood collection time | Plasmin activity in blood ($\Delta A_{405} \times 10^3$/min) | Clot lysis time (hr) |
|---|---|---|---|
| Administration group (10 mg/kg) | 10 min | 9.6 | 3.7 |
| | 30 min | 6.2 | 5.3 |
| | 1 hr | 6.7 | 6.2 |
| | 2 hr | 4.7 | 9.5 |
| Administration group (3 mg/kg) | 10 min | 6.6 | 5.9 |
| | 30 min | 3.0 | 9.5 |
| | 1 hr | 2.1 | >10 |
| | 2 hr | 1.7 | >10 |
| Control group | 10 min | 0.9 | >10 |
| | 30 min | 1.5 | >10 |
| | 1 hr | 1.6 | >10 |
| | 2 hr | 1.7 | >10 |

As seen from Table 4, plasmin activities in blood of the administration group were increased with increase in the doses and reached to, at highest, 6.8 times as high as those of the control group.

EXAMPLE 5

Enhancement of plasmin activity by sustained intravenous injection into rabbits

The compound obtained in Preparation 1 was suspended and dissolved in physiological saline containing 25% ethanol in a concentration of 10 mg/5 ml. 1 mg/0.5 ml of the solution was administered intravenously to rabbits (3 rabbits/group) anesthetized with urethane and sodium pentobarbital, and the remaining 9 mg/4.5 ml was injected over 1 hour by sustained intravenous injection. Blood was collected 10, 30, 60, 90 and 120 minutes after administration of the bolus and the plasmin activity in blood was determined. The average values of the results are shown in Table 5.

TABLE 5

| | Blood collection time (min) | Plasmin activity in blood ($\Delta A_{405} \times 10^3$/min) |
|---|---|---|
| Administration group (10 mg) | 10 | 3.8 |
| | 30 | 7.9 |
| | 60 | 7.3 |
| | 90 | 7.2 |
| | 120 | 8.9 |

TABLE 5-continued

| | Blood collection time (min) | Plasmin activity in blood ($\Delta A_{405} \times 10^3$/min) |
|---|---|---|
| Control group | 10 | 2.6 |
| | 30 | 2.6 |
| | 60 | 2.0 |
| | 90 | 2.7 |
| | 120 | 2.4 |

As seen from Table 5, the plasmin activities of the administration group are 1.4 to 3.7 times as high as those of the control group.

EXAMPLE 6

The compound obtained in Preparation 1 (500 mg), lactose (195 mg) and magnesium stearate (5 mg) were uniformly mixed according to the conventional method and the mixture was filled in a hard gelatin capsule to obtain a capsule.

EXAMPLE 7

The compound obtained in Preparation 1 was dissolved in a mixed solution of 15% of ethanol and 85% of polyethylene glycol 400 in a concentration of 5 mg/ml. The solution was diluted 5-fold with physiological saline containing 0.1% Tween 80 to obtain a solubilized preparation.

What is claimed is:

1. A pharmaceutical composition for preventing and treating thrombosis which comprises a compound of the formula:

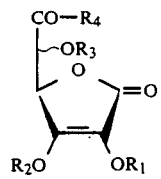

in an amount which is effective for preventing or treating thrombosis, and a pharmaceutically acceptable carrier, wherein $R_1$ and $R_2$ are the same or different and represent hydrogen, or a straight, branched or cyclic $C_{6-24}$ alkyl group or $C_{7-24}$ aralkyl group which may be substituted with a halogen, carboxyl or its ester, carbamoyl, amino, hydroxyl, phenyl, nitro, cyano, $C_{1-4}$ alkoxy, $C_{1-4}$ alkyl or halogeno-$C_{1-4}$ alkyl, provided that at least one of $R_1$ and $R_2$ is not hydrogen;

$R_3$ is hydrogen or an acyl group;

$R_4$ is $OR_5$, $SR_6$ or $NR_7R_8$, wherein $R_5$ and $R_6$ are the same or different and represents a straight or branched $C_{1-24}$ alkyl, $C_{3-8}$ cycloalkyl, $C_{2-24}$ alkenyl, $C_{2-24}$ alkynyl, $C_{7-24}$ aralkyl or $C_{5-24}$ aryl group which may be substituted with a halogen, carboxyl or its ester, carbamoyl, amino, hydroxyl, phenyl, nitro, cyano, $C_{1-4}$ alkoxy, $C_{1-4}$ alkyl or halogeno-$C_{1-4}$ alkyl, and $R_7$ and $R_8$ are the same or different and represent a hydrogen, or a straight or branched $C_{1-24}$ alkyl, $C_{3-8}$ cycloalkyl, $C_{2-24}$ alkenyl, $C_{2-24}$ alkynyl, $C_{7-24}$ aralkyl or $C_{5-24}$ aryl group which may be substituted with a halogen, carboxyl or its ester, carbamoyl, amino, hydroxyl, phenyl, nitro, cyano, $C_{1-4}$ alkoxy, $C_{1-4}$ alkyl or halogeno-$C_{1-4}$ alkyl, or $R_7$ and $R_8$ may together form —$(CH_2)n$—, wherein n is an integer of 4 to 7; and $OR^3$ represents the absolute configuration of R or S.

2. A pharmaceutical composition according to claim 1, wherein $R_4$ is $OR_5$ and wherein $R_5$ is a straight or branched $C_{1-24}$ alkyl, $C_{3-8}$ cycloalkyl, $C_{2-24}$ alkenyl, $C_{2-24}$ alkynyl, $C_{7-24}$ aralkyl or $C_{5-24}$ aryl group which may be substituted with a halogen, carboxyl or its ester, carbamoyl, amino, hydroxy, phenyl, nitro, cyano, $C_{1-4}$ alkoxy, $C_{1-4}$ alkyl or halogeno-$C_{1-4}$ alkyl.

3. A pharmaceutical composition according to claim 1, wherein $R_4$ is $SR_6$ and wherein $R_6$ is a straight or branched $C_{1-24}$ alkyl, $C_{3-8}$ cycloalkyl, $C_{2-24}$ alkenyl, $C_{2-24}$ alkynyl, $C_{7-24}$ aralkyl or $C_{5-24}$ aryl group which may be substituted with a halogen, carboxyl or its ester, carbamoyl, amino, hydroxy, phenyl, nitro, cyano, $C_{1-4}$ alkoxy, $C_{1-4}$ alkyl or halogeno-$C_{1-4}$ alkyl.

4. A pharmaceutical composition according to claim 1, wherein $R_4$ is $NR_7R_8$ and wherein $R_7$ and $R_8$ are the same or different and represent hydrogen or a straight or branched $C_{1-24}$ alkyl, $C_{3-8}$ cycloalkyl, $C_{2-24}$ alkenyl, $C_{2-24}$ alkynyl, $C_{7-24}$ aralkyl or $C_{5-24}$ aryl group which may be substituted with a halogen, carboxyl or its ester, carbamoyl, amino, hydroxy, phenyl, nitro, cyano, $C_{1-4}$ alkoxy, $C_{1-4}$ alkyl or halogeno-$C_{1-4}$ alkyl, or $R_7$ and $R_8$ may together form —$(CH_2)_n$—, wherein n is an integer of 4 to 7.

5. A pharmaceutical composition according to claim 1, wherein at least one of $R_1$ and $R_2$ is a benzyl which may be substituted with a halogen, carboxyl or its ester, carbamoyl, amino, hydroxy, phenyl, nitro, cyano, $C_{1-4}$ alkoxy, $C_{1-4}$ alkyl or halogeno-$C_{1-4}$ alkyl.

6. A pharmaceutical composition according to claim 5, wherein the compound is 2,3-di-O-benzyl-D-glucosaccharoascorbic acid n-octadecanethiolester.

7. A pharmaceutical composition according to claim 5, wherein the compound is 5-O-acetyl-2,3-di-O-benzyl-D-glucosaccharoascorbic acid n-octadecylamide.

8. A pharmaceutical composition according to claim 5, wherein the compound is 2,3-di-O-benzyl-D-glucosaccharoascorbic acid n-octadecylamide.

* * * * *